US00PP19881P2

(12) United States Plant Patent
Klemm

(10) Patent No.: US PP19,881 P2
(45) Date of Patent: Mar. 31, 2009

(54) ***CALIBRACHOA* PLANT NAMED 'KLECA07153'**

(50) Latin Name: *Calibrachoa hybrid*
Varietal Denomination: KLECA07153

(75) Inventor: Nils Klemm, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/079,985

(22) Filed: Mar. 31, 2008

(51) Int. Cl.
*A01H 5/00* (2006.01)

(52) U.S. Cl. ..... Plt./413
(58) Field of Classification Search ..... Plt./413, Plt./263
See application file for complete search history.

*Primary Examiner*—Annette H Para
(74) *Attorney, Agent, or Firm*—Jondle & Associates, P.C.

(57) ABSTRACT

A new *Calibrachoa* plant particularly distinguished by large, red flowers, very strong branching with a mounding and semi-trailing plant habit and a floriferous flowering habit, is disclosed.

1 Drawing Sheet

Genus and species: *Calibrachoa* hybrid.
Variety denomination: 'KLECA07153'.

BACKGROUND OF THE NEW PLANT

The present invention comprises a new and distinct cultivar of *Calibrachoa,* botanically known as *Calibrachoa* hybrid and hereinafter referred to by the cultivar name 'KLECA07153'. The new cultivar originated from a hybridization made in summer 2004 in Stuttgart, Germany. The female parent was the proprietary *Calibrachoa* plant 'W 168' (unpatented), while the male parent was the proprietary *Calibrachoa* plant 'J 003' (unpatented).

The new cultivar was created in May 2005 in Stuttgart, Germany and has been asexually reproduced by vegetative cuttings and tissue culture in Stuttgart, Germany over a two and one-half year period (for more than 35 generations). The present invention has been found to retain its distinctive characteristics through successive asexual propagations.

SUMMARY OF THE INVENTION

The following are the most outstanding and distinguishing characteristics of this new cultivar when grown under normal horticultural practices in Stuttgart, Germany.

1. Large, red flowers;
2. Very strong branching with a mounding and semi-trailing plant habit; and
3. A floriferous flowering habit.

DESCRIPTION OF THE PHOTOGRAPH

This new *Calibrachoa* plant is illustrated by the accompanying photograph which shows flowers and foliage of the plant; the colors shown are as true as can be reasonably obtained by conventional photographic procedures. The photograph is of a five-month-old *Calibrachoa* plant, grown in a greenhouse in Stuttgart, Germany, between January and May 2007.

DESCRIPTION OF THE NEW CULTIVAR

The following detailed descriptions set forth the distinctive characteristics of 'KLECA07153'. The data which defines these characteristics were collected from asexual reproductions carried out in Stuttgart, Germany. The plant history was taken on five-month-old plants which were planted as rooted cuttings in 11-cm pots between January and May 2007 and then grown in a greenhouse. The plants had one terminal pinch one week after potting. Color readings were taken under natural light. Color references are primarily to the R.H.S. Colour Chart of The Royal Horticultural Society of London (R.H.S.) (2001).

DETAILED BOTANICAL DESCRIPTION OF THE NEW PLANT

Classification:
- *Family.*—*Solanaceae.*
- *Botanical.*—*Calibrachoa* hybrid.
- *Common.*—*Calibrachoa.*

Parentage:
- *Female.*—The proprietary *Calibrachoa* plant 'W 168' (unpatented), having yellow flowers with red eyes.
- *Male.*—Violet-flowered proprietary *Calibrachoa* plant 'J 003' (unpatented), having yellow flowers with red veins.

Growth:
- *Form.*—Mounding.
- *Habit.*—Semi-trailing.
- *Height* (*measured from the top of the soil*).—16 cm.
- *Width* (*horizontal plant diameter*).—19 cm.
- *Time to produce a finished flowering plant.*—12 weeks.
- *Outdoor plant performance.*—Very healthy, continuous flowering.
- *Time to initiate and develop roots.*—18 days.
- *Root description.*—Dense and freely branching with white roots.

Stems:
- *Length of basal branches.*—11 cm.
- *Internode length.*—1.0 cm to 1.5 cm.
- *Diameter of branches* (*from midpoint*).—2 cm to 6 cm.

*Stem color.*—RHS 145A.
*Texture.*—Smooth.
*Anthocyanin.*—Absent.
*Pedicel.*—Color: RHS 144B. Length: 1.6 cm. Diameter: 0.2 cm. Texture: Smooth.

Leaves:
*Arrangement.*—Alternate.
*Size.*—Length: 1 cm to 4 cm. Width: 0.5 cm to 2.5 cm.
*Shape.*—Lanceolate to elliptic.
*Apex.*—Broadly acute.
*Base.*—Attenuate.
*Margin.*—Entire.
*Color* (*both immature and mature*).—Upper surface: RHS 137A. Lower surface: RHS 137C.
*Texture* (*both surfaces*).—Smooth.
*Venation.*—Pinnate.
*Venation color (*both surfaces).—RHS 144A.
*Petioles.*—Absent.

Flower bud:
*Shape.*—Irregular to oblong.
*Size.*—Length: 1.8 cm. Diameter: 0.5 cm.
*Color at tight bud.*—RHS 41D.

Inflorescence:
*Blooming habit.*—Continuous flowering, floriferous.
*Inflorescence type.*—Single.
*Floret type.*—Funnel-shaped.
*Lastingness of individual blooms on the plant.*—7 days.
*Fragrance.*—Absent.

Flowers:
*Immature flower.*—Diameter: Horizontal: 2.5 cm. Vertical: 2.4 cm. Color: Upper surface: RHS 41C. Lower surface: RHS 41D.
*Mature flower.*—Diameter: Horizontal: 2.7 cm. Vertical: 2.5 cm. Color: Upper surface: RHS 41C. Lower surface: RHS 41D.
*Corolla tube.*—Color inside: RHS 1A. Color outside: RHS 1B. Tube length: 1.6 cm. Outside texture: Smooth.
*Petals.*—Apex: Obverse. Base: Fused into a tube. Margin: Entire. Waviness of petals: Weak. Lobation: Weak. Texture (both surfaces): Smooth.
*Sepals.*—Calyx (form): Rosette. Shape: Lanceolate to elliptic. Apex: Acute. Base: Fused into a tube. Margin: Entire. Length: 1.4 cm. Width: 0.3 cm. Color: Upper surface: RHS 138A Lower surface: RHS 138B. Texture (both surfaces): Smooth.

Reproductive organs:
*Stamens.*—Number: 5. Filament color: RHS 154A. Filament length: 0.7 cm. Filament diameter: 0.1 cm. Pollen color: RHS 11A. Pollen quantity: Sparse.
*Pistils.*—Number 1. Length: 0.2 cm. Diameter: 0.2 cm. Stigma color: RHS 149A. Style color: RHS 149A.

Fruit and seed set: No seed set observed

Disease and insect resistance: No particular resistance or susceptibility has been observed.

COMPARISON WITH PARENTAL AND COMMERCIAL CULTIVARS

'KLECA07153' differs from the female parent 'W 168' (unpatented) in that 'KLECA07153' has red flowers, while 'W 168' has yellow flowers with red eyes.

'KLECA07153' differs from the male parent 'J 003' in that 'KLECA07153' has red flowers, while 'J 003' yellow flowers with red veins.

'KLECA07153' differs from the commercial cultivar 'KLEC02004' (unpatented) in that 'KLECA07153' has less branching and smaller flowers than 'KLEC02004'.

I claim:

1. A new and distinct cultivar of *Calibrachoa* plant as shown and described herein.

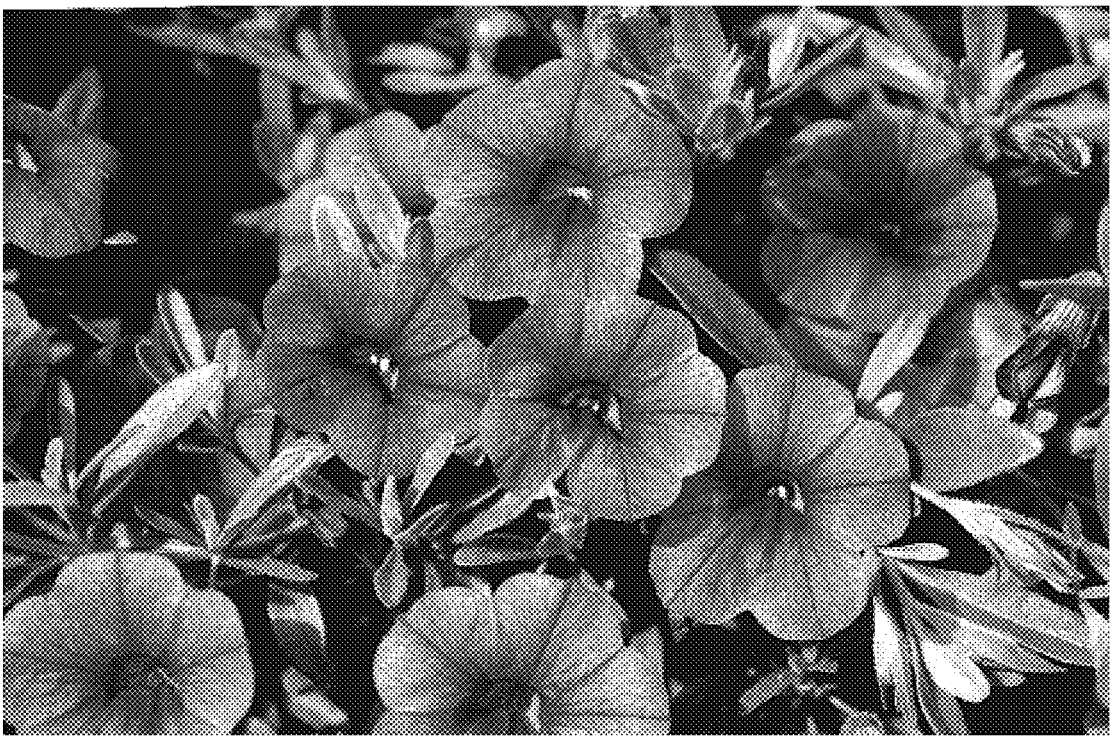

* * * * *